United States Patent
Aono

(10) Patent No.: US 9,274,030 B2
(45) Date of Patent: Mar. 1, 2016

(54) SAMPLE INTRODUCTION DEVICE INCLUDING CHANNEL SWITCHING MECHANISM

(71) Applicant: SHIMADZU CORPORATION, Kyoto-shi, Kyoto (JP)

(72) Inventor: Akira Aono, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 164 days.

(21) Appl. No.: 14/169,733

(22) Filed: Jan. 31, 2014

(65) Prior Publication Data

US 2015/0219532 A1  Aug. 6, 2015

(51) Int. Cl.
*G01N 1/22* (2006.01)
*G01N 30/12* (2006.01)
*G01N 30/02* (2006.01)

(52) U.S. Cl.
CPC .............. *G01N 1/2202* (2013.01); *G01N 30/12* (2013.01); *G01N 2001/2282* (2013.01); *G01N 2030/025* (2013.01); *G01N 2030/128* (2013.01)

(58) Field of Classification Search
CPC ... G01N 30/02; G01N 1/22; G01N 2030/025; G01N 1/2202; G01N 2030/202; G01N 2030/207; G01N 30/44; G01N 2001/2282; G01N 2030/128
USPC .......... 73/23.42, 61.55, 61.56, 863.12; 95/87, 95/89; 96/101, 104–106
See application file for complete search history.

(56) References Cited

U.S. PATENT DOCUMENTS

| | | | | |
|---|---|---|---|---|
| 6,029,499 A | * | 2/2000 | Sittler | G01N 30/88 73/23.42 |
| 7,662,630 B2 | | 2/2010 | Tipler et al. | |
| 2009/0007624 A1 | * | 1/2009 | Bade | G01N 35/1097 73/1.16 |
| 2010/0107730 A1 | * | 5/2010 | Aono | G01N 30/12 73/23.39 |
| 2011/0247394 A1 | * | 10/2011 | McBrady | G01N 30/06 73/23.41 |

* cited by examiner

*Primary Examiner* — Peter Macchiarolo
*Assistant Examiner* — David L Singer
(74) *Attorney, Agent, or Firm* — Sughrue Mion, PLLC

(57) ABSTRACT

A sample introduction device having a channel configuration which allows recapture of samples and in which thorough purging is performed so that no sample components remain inside the channel. In the trap capture process, a first six-way switching valve is placed in state where ports a-f, b-c and d-e are connected, a second six-way switching valve is placed in state where ports a-b, c-d and e-f are connected, and an electromagnetic valve is opened. Carrier gas is introduced through a carrier gas channel, and is discharged via the first six-way valve-sample channel-second six-way switching valve-trap channel-second six-way switching valve-channel-first six-way valve-discharge channel. Carrier gas is also introduced through the path going through the electronic control flow controller, so the operation of stabilization of the analysis channel continues to be performed.

2 Claims, 6 Drawing Sheets

SAMPLE INTRODUCTION DEVICE INCLUDING CHANNEL SWITCHING MECHANISM

CROSS-REFERENCE TO RELATED APPLICATIONS

The entire contents of Japanese Patent Publication No. 2013-053974 to the same inventors, published Mar. 21, 2013, are incorporated herein by reference.

TECHNICAL FIELD

The present invention relates to a thermal desorption type sample introduction device in which a sample tube filled with an adsorbent and a solid sample is heated to cause desorption of a gaseous sample, and the desorbed gaseous sample is introduced into an analytical device such as a gas chromatograph.

BACKGROUND ART

A thermal desorption type sample introduction device which introduces samples into an analytical device such as a gas chromatograph is a device which heats a sample tube filled with an adsorbent and solid sample in order to volatilize the adsorbed components, and introduces them through a transfer line into the column of the gas chromatograph.

In this sort of sample introduction device, if the sample tube is connected directly to the column to introduce the sample components into the column, since the volume of the adsorbent with which the sample column is filled is large while the flow rate inside the column is low, there is the problem that it takes a long time for all the components to pass through the column, and the detection peak bandwidth becomes wide. Thus, a method is employed whereby a trap including a tube filled with a small amount of adsorbent is provided inside the device, and a gas containing the sample components desorbed from the sample tube is passed through the cooled trap to cause adsorption of the components onto the trap, after which the trap is heated to again desorb the sample components and introduce them into the analytical column.

There are devices in which, when introducing the sample components desorbed from the trap into the analytical column, in order to narrow the detection peak bandwidth, only a portion of the gas containing the sample components desorbed from the trap is introduced into the analytical column. Such devices include devices wherein the channels are configured so as to return the split gas which was not introduced into the analytical column to the sample tube side, making it possible to recapture the sample components in the sample tube and reuse them for the next analysis (see Patent Literature 1).

An example of the channel configuration of a sample introduction device for a gas chromatograph including a function of performing recapture of samples will be explained using FIGS. 5A and 5B.

A carrier gas channel 112 for introducing carrier gas is provided. The carrier gas channel 112 branches into channel 114 and channel 118. One of the channels 114 which branches from the carrier gas channel 112 branches further into sample channel 106 and recaptured gas discharge channel 122. A stop valve 116 is provided in channel 114, allowing the channel to be opened and closed. Sample channel 106 is connected to one port of rotary valve 102. Furthermore, a sample tube 104 is arranged in sample channel 106. The sample tube 104 can be heated or cooled by a temperature regulation mechanism 105. A stop valve 124 is arranged in recaptured gas discharge channel 122.

One end of trap channel 110 and one end of sample introduction channel 132 are connected to the other port of rotary valve 102. A captured gas discharge channel 136 and sample introduction gas supply channel 126 are connected to the other end of trap channel 110. The other end of sample introduction channel 132 is connected to a joint 130. A trap column 108 is arranged in the trap channel 110. The trap column 108 can be heated or cooled by a temperature regulation mechanism 109. A stop valve 138 is arranged in captured gas discharge channel 136.

The other channel 118 branched from the carrier gas channel 112 is connected to one port of a three-way valve 120. Channel 128, which leads to sample introduction gas supply channel 126 and joint 130, is connected to the two remaining ports of the three-way valve. Channel 118 is switched and connected to one of sample introduction gas supply channel 126 or channel 128 by the three-way valve. Analysis channel 134 is also connected to joint 130.

Rotary valve 102 can be placed into a state in which sample channel 106 and trap channel 110 are connected (the state of FIG. 5A), and with a different timing, can be placed into a state in which sample channel 106, trap channel 110 and sample introduction channel 132 are connected (the state of FIG. 5B).

The thick line in FIG. 5A is the path along which the carrier gas flows during the process of capturing the sample from sample tube 104 in trap column 108 (hereinafter, the trap capture process). The channels are configured such that, in the trap capture process, a portion of the carrier gas from the carrier gas channel 112 flows through channel 114-sample channel 104-trap channel 110-capture gas discharge channel 136, and the rest of the carrier gas flows through channel 118-channel 128-analysis channel 134. Here, the sample tube 104 is heated to a set temperature by temperature regulation mechanism 105, and the trap column 108 is cooled to a set temperature by temperature regulation mechanism 109. As a result, the sample from the sample tube 104 is desorbed and flows together with the carrier gas, and that sample is captured in trap column 108.

The thick line in FIG. 5B is the path along which the carrier gas flows during the process in which a portion of the sample captured in trap column 108 is introduced into the analytical column and the rest of the sample is recaptured in the sample tube 104 (the sample introduction and recapture process). In the sample introduction and recapture process, the carrier gas from the carrier gas channel 112 passes through channel 118 and channel 126 and flows through trap channel 110. Here, the trap column 110 is heated to a set temperature by temperature regulation mechanism 109, and sample tube 104 is cooled to a set temperature by the temperature regulation mechanism. The desorbed sample from the trap column 110 flows along with carrier gas to rotary valve 102. The rotary valve 102 is switched to a state in which sample channel 106, trap channel 110 and sample introduction channel 132 are connected. Gas containing the sample desorbed from trap column 110 is split via joint 130 to the sample introduction channel 132 side connected to analysis channel 134 and to the sample channel 106 side. As a result, a portion of the sample desorbed from the trap column 108 passes through analysis channel 134 and is guided to the analytical column of the chromatograph, and the rest of the sample is recaptured in the sample tube 104.

PRIOR ART LITERATURES (Patent literature 1) U.S. Pat. No. 7,662,630

SUMMARY OF THE INVENTION

In the channel configuration of FIGS. 5A and 5B, gas flows into the sample introduction channel 132 between rotary valve 102 and joint 130 only during the sample introduction and recapture process. Thus, there is the problem that thorough purging of the inside of the sample introduction channel 132 is not achieved, and if the sample contains high boiling point components, the high boiling point components will remain in this section and will end up being carried over to the next analysis.

Thus, it is an object of the present invention to provide a sample introduction device having a channel configuration which allows recapture of samples and in which thorough purging is performed so that no sample components remain inside the channel.

The present invention is a sample introduction device including: a sample channel in which a sample tube wherein a sample has been captured is arranged; a sample tube temperature regulation mechanism which performs heating and cooling of said sample tube; a trap channel including a trap column for capturing sample desorbed from the sample tube; a trap temperature regulation mechanism which performs heating and cooling of the trap column; a sample introduction channel whereof one end is connected to an analysis channel including an analytical column for performing separation of samples and a detector for detecting sample components separated in the analytical column; a splitter which is arranged upstream of the analytical column in the sample introduction channel and which has a first and second split outlets which split and feed out the supplied gas, wherein the first split outlet is connected to the analytical column; a first carrier gas supply channel which supplies carrier gas for transporting the sample from the sample tube to the trap column; a second carrier gas supply channel which supplies carrier gas for transporting the sample captured in the trap column to the analysis channel simultaneously with or at a different timing from the first carrier gas supply channel; and a channel switching mechanism which allows switching between a trap capture state in which the sample channel and trap channel are connected from the upstream side to downstream of the first carrier supply channel and the sample introduction channel is connected to downstream of the second carrier gas supply channel, and a sample introduction and recapture state in which the trap channel and sample introduction channel are connected from the upstream side to downstream of the second carrier gas supply channel and the sample channel is connected to the second split outlet of the splitter.

According to the present invention, the channel switching mechanism allows a trap capture state to be assumed in which the sample channel and trap channel are connected from the upstream side to downstream of the first carrier gas supply channel and the sample introduction channel is connected to downstream of the second carrier gas supply channel, thus making it possible to allow carrier gas to flow into the sample introduction channel from the second carrier gas supply channel during the trap capture process in which the sample is desorbed from the sample tube and captured in the trap column. In the conventional channel configuration shown in FIG. 5, the sample introduction channel 132 is a dead end, and during the trap capture process, gas does not flow through this sample introduction channel 132, so the sample introduction channel 132 is not thoroughly purged, and sample from the previous measurement remains in the sample introduction channel 132 and may affect the measurement results. By contrast, in the channel configuration of the present invention, no such dead-end part is present, so samples from previous measurements are prevented from affecting the measurement.

DETAILED DESCRIPTION OF THE EXEMPLARY EMBODIMENTS

In a preferable mode of embodiment of the sample introduction device of the present invention, the first carrier gas supply channel and second carrier gas supply channel supply carrier gas from a common carrier gas supply source. As a result, it is possible to have a single carrier gas supply source and achieve a reduction in cost of the device configuration.

Figure 1:
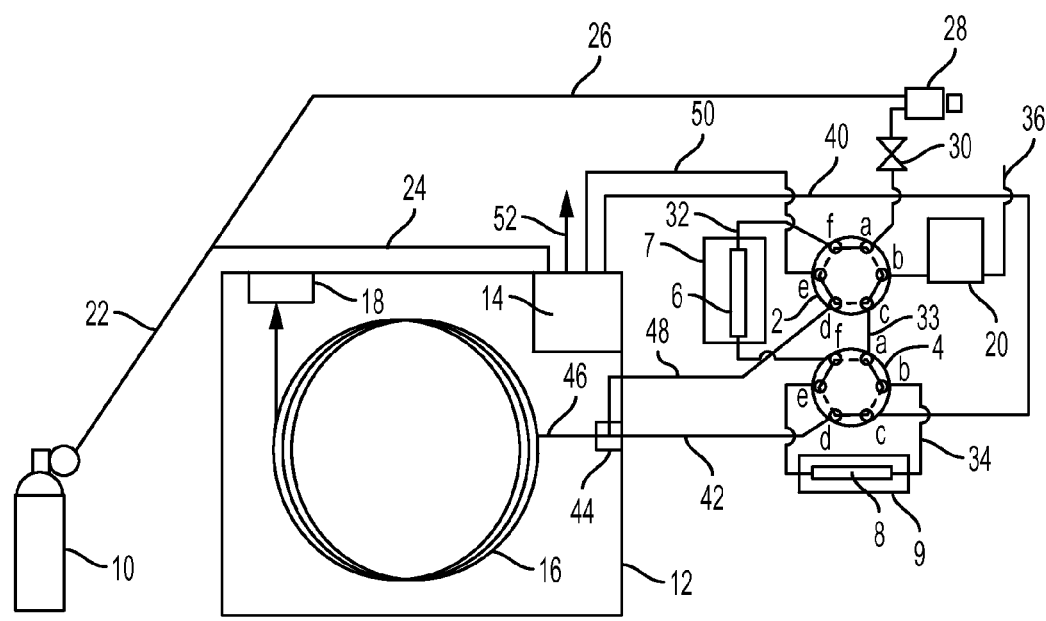
FIG. 1 is a channel configuration diagram schematically illustrating an example of embodiment of a gas chromatograph including a sample introduction device.

An example of a gas chromatograph including a sample introduction device of one example of embodiment will be described using FIG. 1.

In this gas chromatograph, the sample in the sample tube 6 is captured temporarily in a trap column 8, and a portion of the sample captured in the trap column 8 is introduced into analytical unit 12 to perform analysis. The analytical unit 12 comprises an analytical column 16 and a detector 18. The sample introduction unit of this example of embodiment, for introducing the sample into the analytical unit 12, comprises two six-way switching valves 2 and 4, and the channel appropriate for each process is configured by switching of these switching valves 2 and 4. The six-way valves 2 and 4 each comprise six ports a through f, and can be placed into a state where ports a-b, c-d and e-f are connected, or a state where ports a-f, b-c and d-e are connected.

Two carrier gas channels 24 and 26 are provided as the channels for supplying carrier gas. These carrier gas channels 24 and 26 are channels which branch off from channel 22, which is connected to a carrier gas tank 10 which is the carrier gas supply source. Carrier gas channel 24 is connected to an electronic control flow controller 14 provided in analytical unit 12, and carrier gas flows through channel 40 while undergoing flow rate control by the electronic control flow controller 14. Channel 40 is connected to port c of six-way switching valve 4. Carrier gas channel 26 is connected to port a of six-way switching valve 2. Pressure regulation valve 28 and electromagnetic valve 30 are provided in channel 26.

Carrier gas channel 26 constitutes a first carrier gas supply channel which supplies carrier gas for transporting the sample from the sample tube 6 to the trap column 8. Carrier gas channel 24 and channel 40 constitute a second carrier gas supply channel which supplies carrier gas for transporting the sample from the trap column 8 to the analytical unit 12.

A discharge channel 36 is connected to port b of six-way switching valve 2. A mass flow meter 20 is provided in the discharge channel 36. Port c is connected via channel 33 to port a of six-way switching valve 4. One end of split channel 48 of analytical unit 12 is connected to port d. The other end of split channel 48 is connected via splitter 44 to subsequently described sample introduction channel 42 and analysis channel 46. Port e is connected via channel 50 to the electronic control flow controller 14 provided in analytical unit 12. One end of sample channel 32 is connected to port f. The other end of sample channel 32 is connected to port f of six-way switching valve 4. A sample tube 6 is arranged in sample channel 32.

It will be noted that in this example of embodiment, the electronic control flow controller 14 is provided in the analytical unit 12, but it is also possible to provide the electronic control flow controller 14 independently of the analytical unit 12.

One end of trap channel 34 is connected to port b of six-way switching valve 4, and the other end of trap channel 34 is connected to port e. Trap column 8 is arranged in trap channel 34. Sample introduction channel 42 is connected to port d of six-way switching valve 4. Sample introduction channel 42 is connected via splitter 44 to split channel 48 and analysis channel 46 of analytical unit 12. Analytical column 16 and detector 18 are provided in analysis channel 46.

A drain 52 is provided in electronic control flow controller 14, and gas which has entered through channel 50 is discharged to the outside through drain 52.

A temperature regulation mechanism 7 for performing heating and cooling of the sample tube 6 is arranged in sample channel 32. Temperature regulation mechanism 7 is controlled so as to heat the sample tube 6 when the sample in the sample tube 6 is to be desorbed, and so as to cool the sample tube 6 when the sample is to be captured in the sample tube 6.

Furthermore, a temperature regulation mechanism 9 for performing heating and cooling of trap column 8 of trap channel 34 is provided. Temperature regulation mechanism 9 is controlled so as to cool the trap column 8 when the sample is to be captured in the trap column 8, and so as to heat the trap column 8 when the sample captured in the trap column 8 is to be desorbed.

The temperature regulation mechanisms 7 and 9 are not particularly limited, but for example, Peltier elements may be used for this purpose.

Next, the operation of the gas chromatograph of the same example of embodiment will be described using FIG. 2 through FIG. 4.

(Standby)

Figure 2:
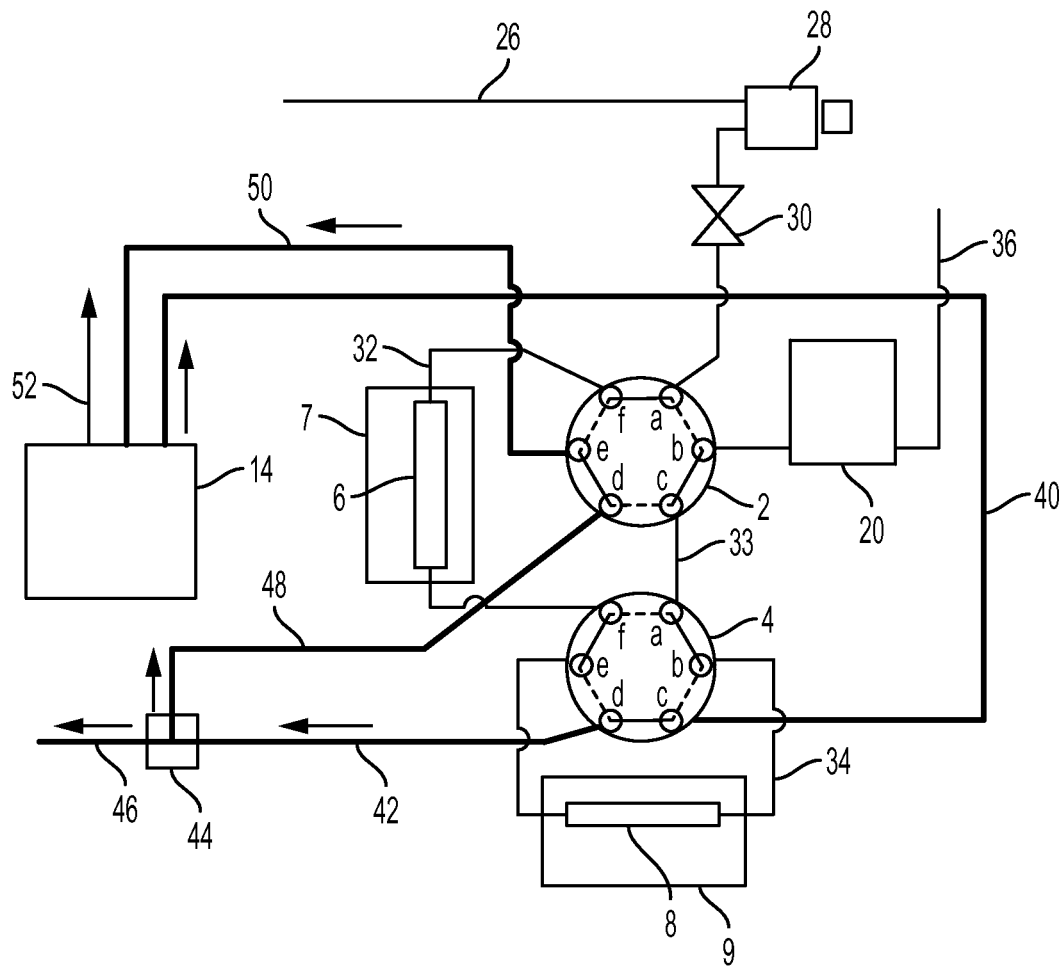
FIG. 2 is a channel diagram intended to explain the flow path of carrier gas in the standby state of the sample introduction device of the same example of embodiment.

FIG. 2 shows the channel configuration in the standby state. In the standby state, the six-way switching valve 2 is placed into a state where ports a-f, b-c and d-e are connected, and six-way switching valve 4 is placed into a state in which ports a-b, c-d and e-f are connected. Electromagnetic valve 30 is kept closed, preventing carrier gas from flowing into sample channel 32 and trap channel 34. Carrier gas is introduced only from carrier gas channel 24 via electronic control flow controller 14, achieving stabilization of the analysis channel 46.

Carrier gas which has been introduced via electronic flow controller 14, as shown by the thick line, passes through channel 40-six-way switching valve 4-sample introduction channel 42, and arrives at splitter 44. Carrier gas which has reached the splitter 44 is divided into gas which flows to the analysis channel 46 side and gas which flows to the split channel 48 side, a portion is discharged through analysis channel 46-analytical column 16-detector 18, and the rest passes through split channel 48-six-way valve 2-channel 50-electronic control flow controller 14, and is discharged from drain 52. In this state, a sample tube 6 is arranged in sample channel 32.

(Trap Capture Process)

Figure 3:
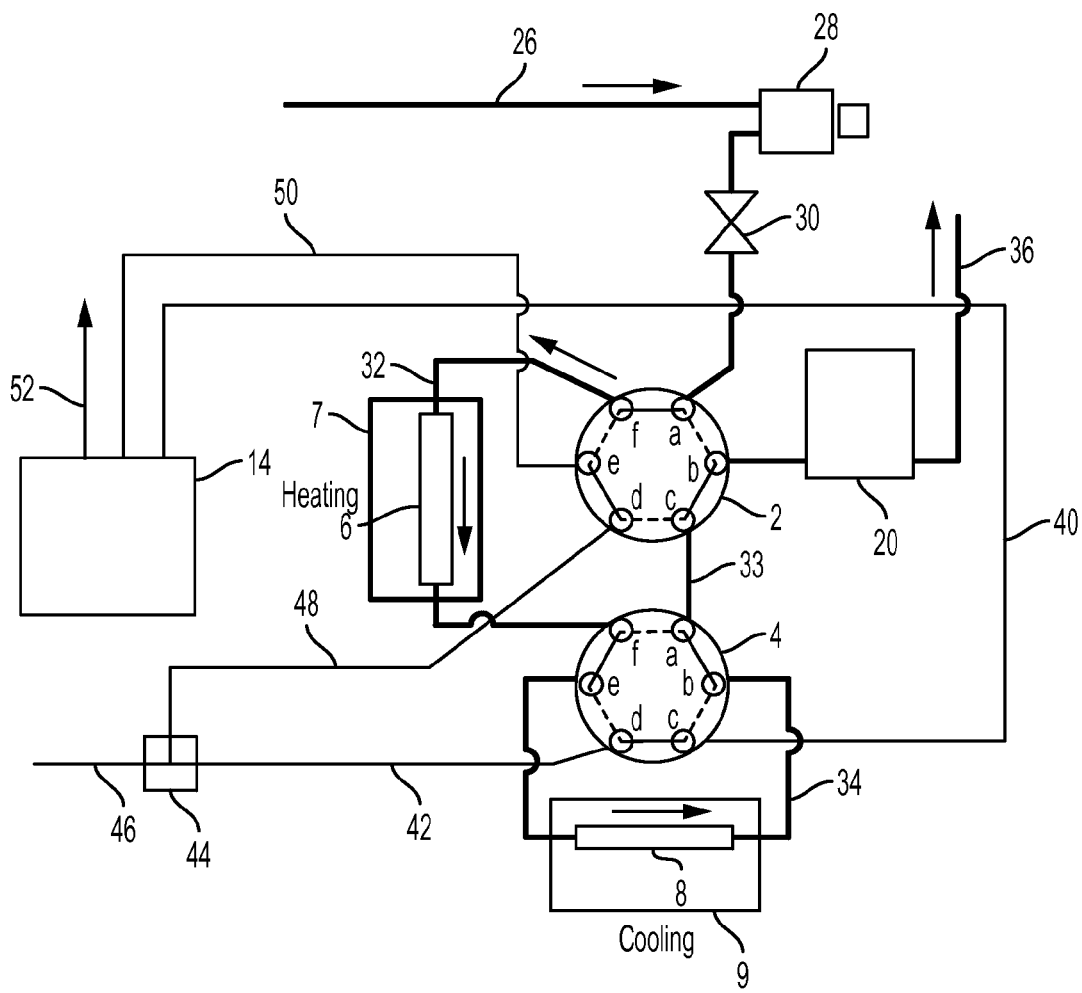
FIG. 3 is a channel diagram showing the flow path of carrier gas in the trap capture process of the sample introduction device of the same example of embodiment.

FIG. 3 shows the channel configuration during the trap capture process.

After the sample tube 6 has been arranged in the sample channel 32, a trap capture process is performed in which the sample is desorbed from the sample tube 6 and is captured in the trap column 8. In the trap capture process, the six-way switching valves 2 and 4 are placed in the same state as the standby state, and electromagnetic valve 30 is opened. Carrier gas is introduced through carrier gas channel 26, and is discharged via six-way valve 2-sample channel 32-six-way switching valve 4-trap channel 34-six-way switching valve 4-channel 33-six-way valve 2-discharge channel 36, as shown by the thick line.

The sample tube 6 is heated for example to 200° C. by temperature regulation mechanism 7, causing the sample which had been adsorbed in the sample tube 6 to be desorbed and carried along with the carrier gas into the trap column 8. Trap column 8 is cooled for example to −20° C. by temperature regulation mechanism 9, and sample desorbed from the sample tube 6 is captured by adsorbing in the trap column 8.

(Sample Introduction and Recapture Process)

Figure 4:
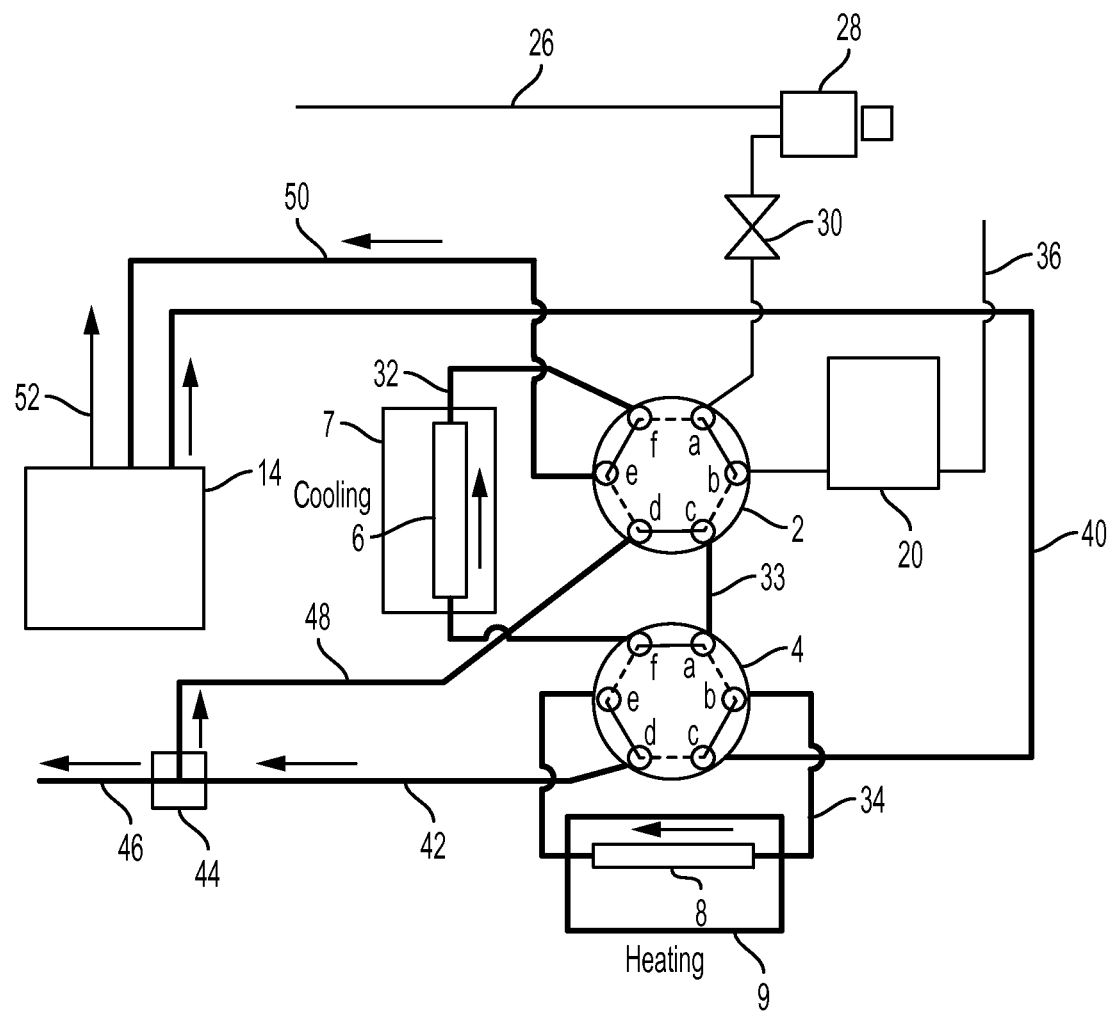
FIG. 4 is a channel diagram showing the flow path of carrier gas in the sample introduction and recapture process of the sample introduction device of the same example of embodiment.

FIG. 4 shows the channel configuration for the sample introduction and recapture process.

After sample has been captured in the trap column 8, a sample introduction and recapture process is performed in which a portion of the captured sample is introduced into the analytical unit 12 and the rest of the sample is recaptured in the sample tube 6. In the sample introduction and recapture process, six-way valve 2 is placed in a state where ports a-b, c-d and e-f are connected and six-way switching valve 4 is placed in state in which ports a-f, b-c and d-e are connected.

The sample tube 6 is cooled for example to 25° C. by temperature regulation mechanism 7, and the trap column 8 is heated for example to 250° C. by temperature regulation mechanism 9. The carrier gas supplied via electronic control flow controller 14 flows through channel 40-six-way switching valve 4-trap channel 34-six-way switching valve 4-sample introduction channel 42 to splitter 44, as shown by the thick line. Here, the sample which had been captured in the trap column 8 is desorbed by heating and transported by the carrier gas.

A portion of the gas containing the sample which has reached the splitter 44 is introduced into the analytical unit 12, passes through analysis channel 46, and is separated into individual components in analytical column 16 and detected by detector 18. The gas containing the rest of the sample passes through split channel 48 and six-way switching valves 2 and 4 and is guided into sample tube 6 of sample channel 33, and the sample contained in that gas is recaptured in the cooled sample tube 6. Carrier gas which has passed through the sample tube 6 passes through six-way valve 2-channel 50-electronic control flow controller 14, and is discharged through drain 52.

In FIG. 3, only the path of channel 26-six-way valve 2-sample channel 32-six-way switching valve 4-trap channel 34-six-way switching valve 4-channel 33-six-way valve 2-discharge channel 36 is shown with a thick line as the path along which the carrier gas flows, but carrier gas is also introduced through the path going through the electronic control flow controller 14, so the operation of stabilization of the analysis channel 46 continues to be performed. Namely, in the trap capture process, carrier gas introduced via electronic control flow controller 14 reaches the splitter 44 through six-way switching valve 4-sample introduction channel 42, and is split into gas which flows to the analysis channel 46 side and gas which flows to the split channel 48 side, a portion is discharged through analysis channel 46-analytical column 16-detector 18, and the rest passes through split channel 48-six-way valve 2-channel 50-electronic control flow controller 14 and is discharged from drain 52.

Figure 5A:
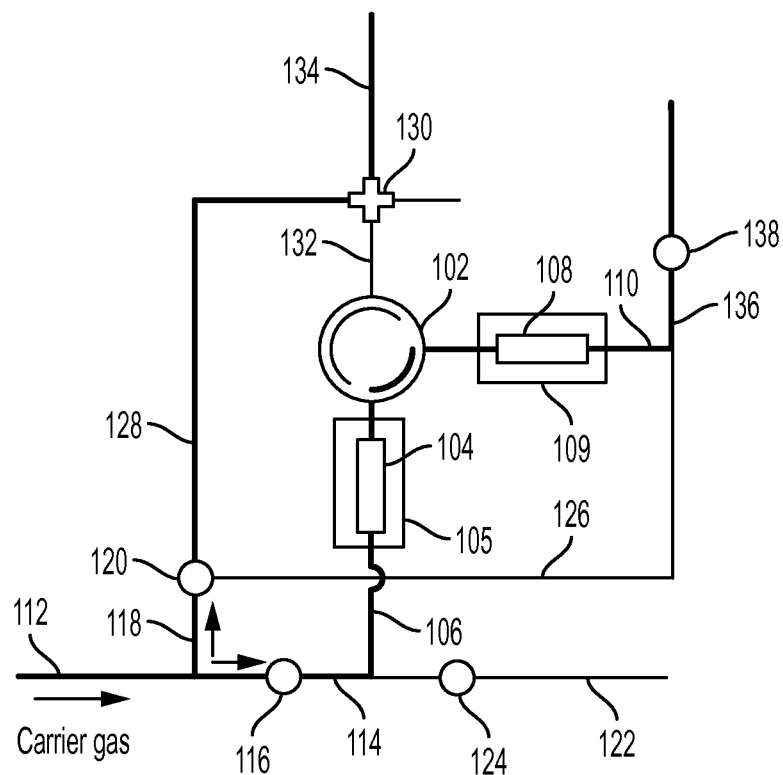
FIGS. 5A and 5B are channel configuration diagrams schematically illustrating an example of the channel configuration of a conventional sample introduction device.
Figure 5B:
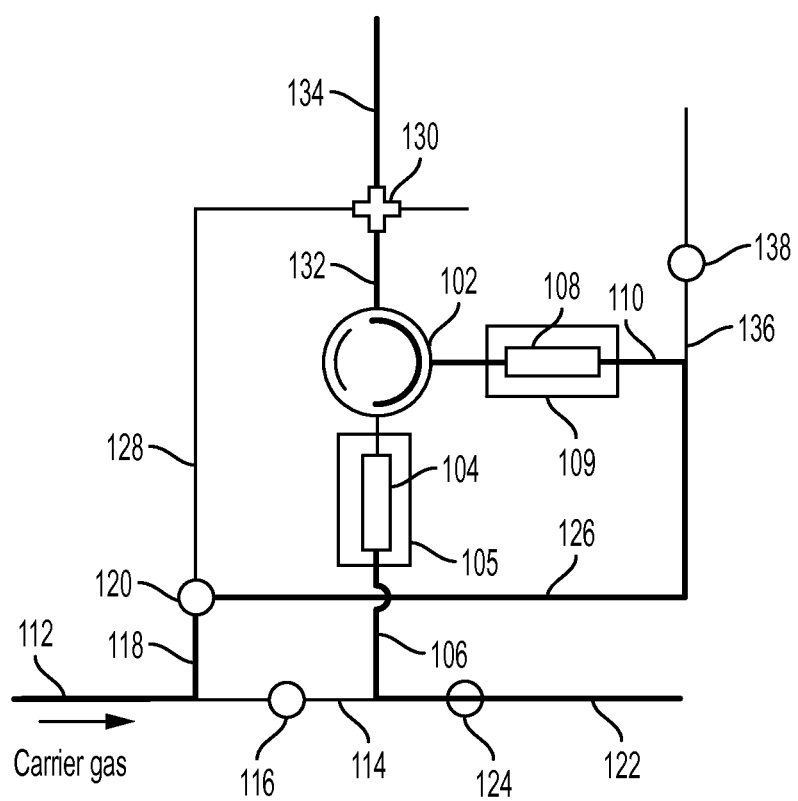

In this way, during the trap capture process as well, carrier gas flows through sample introduction channel 42 and analysis channel 46, which are not involved in the capture of sample in the trap column 8, and is discharged to the outside, so that the inside of the channels not involved in the trap capture process is purged. Namely, in the channel configuration of this example of embodiment, there is no dead-end portion through which gas flows only when sample is introduced from the trap column to the analytical unit side, as in the case of the sample introduction channel 132 in the channel configuration of FIGS. 5A and 5B, and so even if sample from the previous measurement should remain in the channel, that residual sample will be discharge to the outside before the sample introduction and recapture process, and will not be introduced into the analytical column 16 together with the measurement sample.

DESCRIPTION OF REFERENCES 2, 4 Six-Way Valve
6 Sample tube
7 Temperature regulation mechanism (for sample tube)
8 Trap column
9 Temperature regulation mechanism (for trap column)
10 Carrier gas tank
12 Analytical unit
14 Electronic control flow controller
16 Analytical column
18 Detector
24, 26 Carrier gas supply channel
32 Sample channel
34 Trap channel
42 Sample introduction channel
44 Splitter
46 Analysis channel
48 Split channel

What is claimed is:

1. A sample introduction device, comprising:
a sample channel in which a sample tube wherein a sample has been captured is arranged;
a sample tube temperature regulation mechanism which performs heating and cooling of said sample tube;
a trap channel comprising a trap column for capturing sample desorbed from said sample tube;
a trap temperature regulation mechanism which performs heating and cooling of said trap column;
a sample introduction channel whereof one end is connected to an analysis channel comprising an analytical column for performing separation of samples and a detector for detecting sample components separated in the analytical column;
a splitter which is arranged upstream of said analytical column in said sample introduction channel and which has a first and second split outlets which split and feed out the supplied gas, wherein the first split outlet is connected to said analytical column;
a first carrier gas supply channel which supplies carrier gas for transporting the sample from said sample tube to said trap column;
a second carrier gas supply channel which supplies carrier gas for transporting the sample captured in said trap column to said analysis channel simultaneously with or at a different timing from said first carrier gas supply channel; and
a channel switching mechanism which allows switching between a trap capture state in which said sample channel and said trap channel are connected from the upstream side to downstream of said first carrier gas supply channel and said sample introduction channel is connected to downstream of said second carrier gas supply channel, and a sample introduction and recapture state in which said trap channel and said sample introduction channel are connected from the upstream side to downstream of said second carrier gas supply channel and said sample channel is connected to the second split outlet of said splitter.

2. A sample introduction device as described in claim 1, configured such that said first carrier gas supply channel and said second carrier gas supply channel supply carrier gas from a common carrier gas supply source.

* * * * *